(12) United States Patent
Westenberg

(10) Patent No.: US 8,992,624 B2
(45) Date of Patent: Mar. 31, 2015

(54) BONE IMPLANT

(71) Applicant: Gerry Westenberg, Gosford (AU)

(72) Inventor: Gerry Westenberg, Gosford (AU)

(*) Notice: Subject to any disclaimer, the term of this patent is extended or adjusted under 35 U.S.C. 154(b) by 0 days.

(21) Appl. No.: 13/757,469

(22) Filed: Feb. 1, 2013

(65) Prior Publication Data
US 2013/0150966 A1    Jun. 13, 2013

(30) Foreign Application Priority Data

Feb. 15, 2002  (AU) .................... 2012100167

(51) Int. Cl.
A61F 2/38 (2006.01)
A61F 2/30 (2006.01)
A61F 2/28 (2006.01)

(52) U.S. Cl.
CPC ............. *A61F 2/28* (2013.01); *A61F 2/3859* (2013.01); *A61F 2/30* (2013.01); *A61F 2002/30281* (2013.01); *A61F 2002/30332* (2013.01); *A61F 2002/30367* (2013.01); *A61F 2002/30387* (2013.01); *A61F 2002/30395* (2013.01); *A61F 2002/30403* (2013.01); *A61F 2002/30405* (2013.01); *A61F 2002/30408* (2013.01); *A61F 2002/30434* (2013.01); *A61F 2002/30487* (2013.01); *A61F 2002/30492* (2013.01); *A61F 2/30734* (2013.01); *A61F 2002/30426* (2013.01); *A61F 2002/30614* (2013.01); *A61F 2002/30736* (2013.01)
USPC ............... 623/20.15; 623/22.41; 623/22.42

(58) Field of Classification Search
USPC ................. 623/20.15, 22.41, 22.42
See application file for complete search history.

(56) References Cited

U.S. PATENT DOCUMENTS

| 7,293,936 | B1 * | 11/2007 | Warren ............... 403/296 |
| 7,766,969 | B2 * | 8/2010 | Justin et al. ............. 623/20.15 |
| 2006/0142869 | A1 * | 6/2006 | Gross ................. 623/20.34 |
| 2010/0298947 | A1 * | 11/2010 | Unger ................. 623/20.32 |

* cited by examiner

Primary Examiner — Randy Shay
(74) Attorney, Agent, or Firm — Kilpatrick Townsend & Stockton LLP

(57) ABSTRACT

A bone implant including a peg component for fixing the implant into a bone, a body component for abutment with a mating bone implant and a coupling to allow releasable connection between the peg component and the body component.

7 Claims, 5 Drawing Sheets

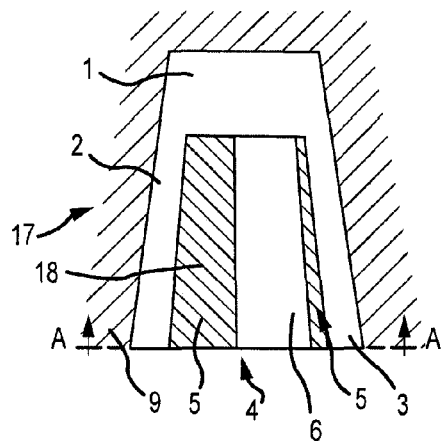
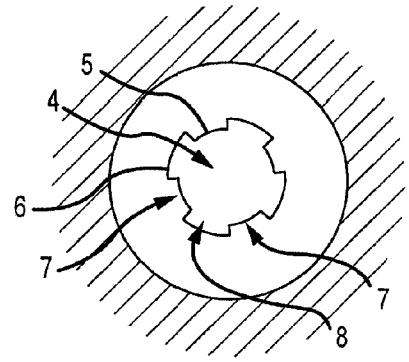
FIG.1  FIG.2
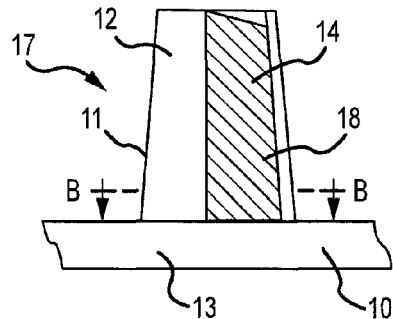
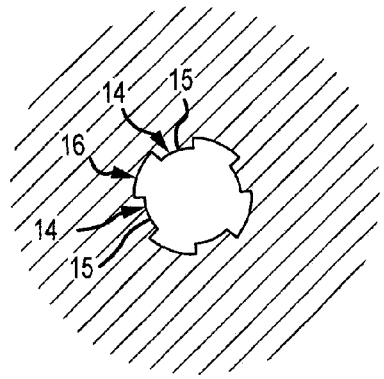
FIG.3  FIG.4

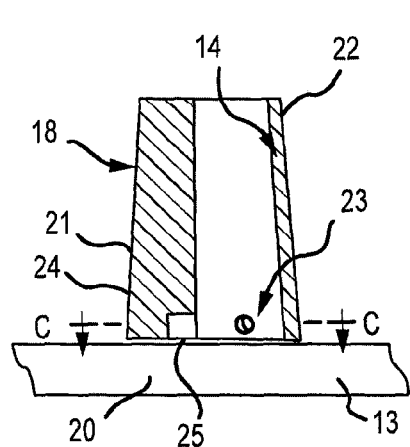
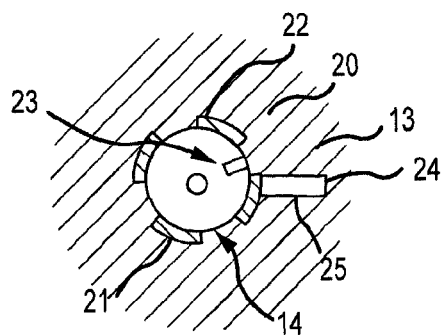
FIG.5
FIG.6
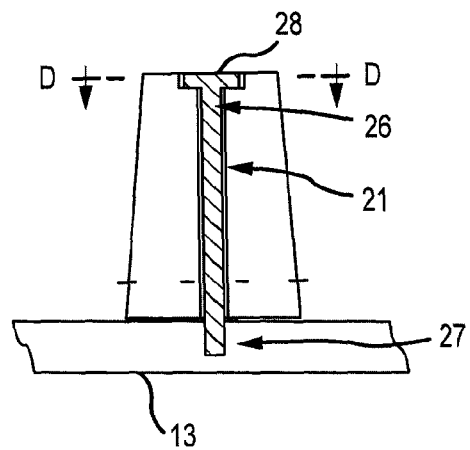
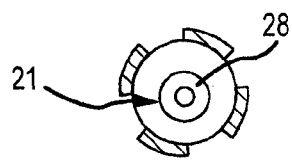
FIG.7
FIG.8

US 8,992,624 B2

BONE IMPLANT

RELATED APPLICATION

This application claims priority from Australian Patent Number 2012100167, the contents of which are incorporated herein by reference.

FIELD OF THE INVENTION

The present invention relates to a bone implant.

BACKGROUND OF THE INVENTION

A bone implant typically includes a peg that can be hammered into a pre-drilled hole to secure the implant into a bone. The implant also includes an integrally formed implant body portion for abutment with a mating bone implant.

One possible application for bone implants is knee reconstruction. The peg of one implant is embedded at a suitable attachment site in the tibia and the peg of the other implant is driven into the femur. The facing body portions of each implant serve to replace the original knee joint.

Implants are also used in hip replacements, where the implants provide a ball and socket joint to replace the original functioning of the hip joint.

In some circumstances, one of the pegs may work loose and the associated hole may need to be re-bored and a larger diameter peg used. Alternatively, the implant might simply need replacing, in which case the bone may need to be broken to release the peg. In either case, the surgical procedure is substantial and invasive. Also, bone dimensions and strength characteristics as well as the use of larger diameter pegs may limit the number of implant replacements.

As a result, only a limited number of implant replacements may be viable and installation of an initial implant is generally deferred for as long as possible in the hope the original implant will last a sufficient amount of time. However, considerable pain and discomfort may be experienced if joint replacement is delayed.

OBJECT OF THE INVENTION

The present invention seeks to provide an improved bone implant.

SUMMARY OF THE INVENTION

In accordance with the present invention, there is provided a bone implant including a peg component for fixing the implant into a bone, a body component for abutment with a mating bone implant and a coupling to allow releasable connection between the peg component and the body component.

Preferably, the coupling includes a male connector and female connector that are moved into engagement by advancing the body component into an engaged condition relative to the peg component.

Preferably, the female connector is in the form of a nut associated with the peg component and the male connector is a bolt associated with the body component.

Preferably, the coupling includes a lock mechanism to secure the components in the engaged condition.

Preferably, the lock mechanism includes an interrupted thread on each of the connectors.

Especially in the case multiple peg implants are used, the lock mechanism preferably further includes an actuator for rotating one of the connectors relative to the other connector in order to drive the interrupted thread on each connector into a locked engagement.

Preferably, the actuator is in the form of a lever arm connected to one of the connectors.

Preferably, the connector with the lever arm is mounted to the associated component via an axle that allows the connector to be rotated into locked engagement with the other connector without requiring the component itself to be rotated.

Preferably, the implant further includes a wedge device to secure the lever arm against reverse rotation once the connectors are rotated into locked engagement.

Preferably, a locking pin is provided to further secure the connectors against reverse rotation out of locked engagement, the locking pin being mounted relative to one of the connectors and being received in a bore formed in the other one of the connectors that aligns with the pin when the connectors are in locked engagement.

Preferably, the locking pin is carried by the wedge device.

Preferably, the bone implant includes a plurality of pairs of connectors for releasably engaging the body component relative to a bone.

In another aspect, there is provided a peg component for use in the above described bone implant, including a connector for releasable engagement with the body component.

In another aspect, there is provided a body component for use in the above described bone implant, including a connector for releasable engagement with the peg component.

BRIEF DESCRIPTION OF THE DRAWINGS

The invention is more fully described, by way of non-limiting example only, with reference to the accompanying drawings, in which:

FIGS. 1 through 4 are for a single peg bone implant such as the lower bone implant for the Tibia. In particular:

FIG. 1 is a diagrammatic cross sectional view of a peg component of a bone implant;

FIG. 2 is a diagrammatic end view of the peg component, taken along the line A-A shown in FIG. 1;

FIG. 3 is a diagrammatic profile view of a joint component;

FIG. 4 is a cross-sectional view, taken along the line B-B shown in FIG. 3;

FIGS. 5 through 13 illustrate connectors suitable for a multiple peg bone implant such as the upper knee implant for the Femur. In particular:

FIG. 5 is a diagrammatic side view of a multiple peg bone implant;

FIG. 6 is a view taken along the line C-C shown in FIG. 5;

FIG. 7 is a cross sectional view of the component of FIG. 5;

FIG. 8 is a view taken along the line D-D shown in FIG. 7;

FIG. 9 is a diagrammatic side view of the peg recess of the bone;

FIG. 10 is a view taken along the line E-E shown in FIG. 9, illustrating the position of a wedge device);

FIG. 13 is a diagrammatic view illustrating the attachment of one of the pegs of the multiple bone implant to a femur.

DETAILED DESCRIPTION OF THE DRAWINGS

Figure 9:
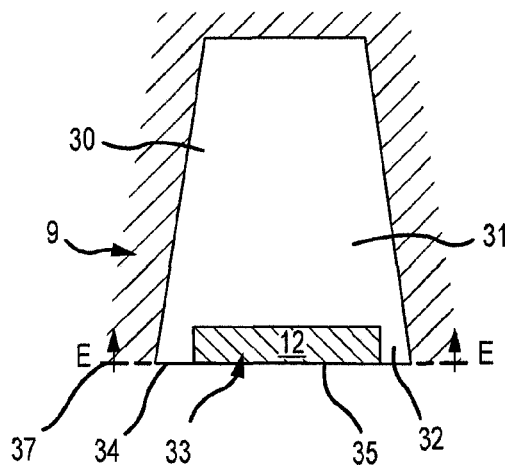

Referring firstly to FIG. 1, a peg component 1 is shown in cross section mounted in bone 9. The component 1 includes a frusto-conical female connector 2 that is in the form of a nut 3 with a central cavity 4. An interrupted thread 5 is provided on an internal wall 6 of the cavity 4.

FIG. 2 illustrates a plan view of the peg component 1. The interrupted thread 5 includes threaded sections 7 that project into the cavity 4. The threaded sections 7 are interrupted by voids 8 arranged at regular intervals.

Referring now to FIG. 3, a body component 10 is shown as including a male connector 11 in the form of a bolt 12 mounted to an implant body 13. The male connector 11 is also frusto-conical in shape to match the corresponding shape of the female connector 2. The male connector 11 is also provided with an interrupted thread 14.

As shown in the sectioned view of FIG. 4, the interrupted thread 14 is formed of threaded sections 15 separated by rebates 16 at regular intervals.

The male connector 11 and female connector 2 together form a coupling 17 (should there be a illustration of 17?) for connecting the peg component 1 to the body component 10. To facilitate connection, the bolt 12 is moved into engagement with the nut 3 by advancing the male connector 11 into the female connector 2 so that the threaded sections 7, 15 of each of the male and female connectors 11, 2 slide axially through the respective voids and rebates 8, 16.

From the engaged condition, the bolt 12 is rotated relative to the nut 3 in order for the interrupted thread 5, 14 of each connector 2, 11 to securely lock the two components 1, 10 together. The interrupted thread 5, 14 on each component 1, 10 thereby forms a lock mechanism 18 to reliably secure the male and female connectors 2, 11 together to form a single bone implant.

An advantage of using interrupted thread 5, 14 as a lock mechanism 18 is only minimal rotation between the components 1, 10 is required to achieve a connection able to withstand substantial axial loads such as may be placed on a bone implant used in a knee reconstruction. Also, the minimal turning required may be advantageous in restricted space conditions, such as where the body component 10 needs to be fitted or removed for replacement in a surgical environment.

If a single peg bone implant needs to be replaced, it is a simple process of turning the body counter-clockwise to disengage the interrupted thread, and remove the bone implant. Replacement with a new bone implant would be as described above.

Referring now to FIGS. 5 and 6, an example of a multiple peg of a body component 20 is illustrated and like reference numerals will be used to denote similar parts to those described above in relation to FIGS. 3 and 4.

The body component 20 includes a male connector 21 or bolt 22 that is rotationally mounted to the implant body 13. The connector 21 further includes a locking pin bore 23 and an actuator 24 in the form of a lever arm 25 that can be manipulated to assist with rotating the connector 21.

FIGS. 7 and 8 show the male connector 21 mounted to the implant body 13 by way of an axle 26 that is threaded into the body 13 at one end 27. An enlarged head 28 is provided at the other end of the axle 26 to hold the connector 21 on the axle 26.

Referring now to FIG. 9, a peg component 30 with a female connector 31 is shown in profile. The female connector 31 is similar to the female connector 2 of FIGS. 1 and 2. Like parts are denoted with like reference numerals.

The female connector 31, in the form of nut 32, has a recess 33 formed adjacent an end 34 of the connector 31 to receive a wedge device 35. The end 34 of the nut 32 is designed to sit flush with a surface 37 of bone 9, in which the peg component 30 is mounted, so the recess 33 has a depth dimension sufficient to accommodate the wedge device 35 whilst maintaining a flush finish with the bone 9.

Figure 10:
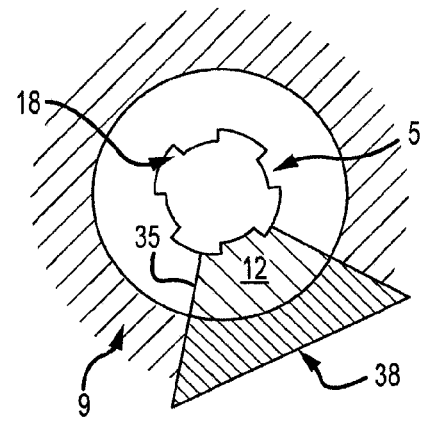

A wedge-shaped region 38 of the bone 9 is also removed, as illustrated in FIG. 10, to fit the wedge device 35.

Figure 11A:
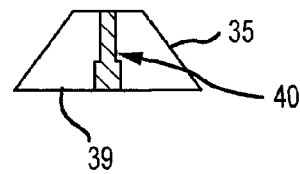
FIG. 11a is a plan view of the wedge device.
Figure 11B:
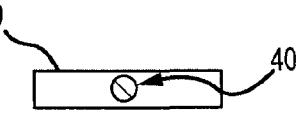
FIG. 11b is a front view of the wedge device.
Figure 11C:
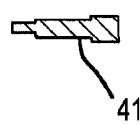
FIG. 11c is a view of a pin used in the wedge device.

Referring to FIG. 11, the wedge device 35 is shown as including a flat wedge piece 39 with a central aperture 40 and a locking pin 41. The locking pin 41 is designed to be screwed into the locking pin bore 23 of the bolt 22 when the male and female connectors 21, 31 are rotated into locking engagement.

More particularly, the two components 20, 30 are designed to be secured together by axially advancing the bolt 22 into the nut 32 and then rotating the bolt 22 using the lever arm 25, which is accessible through the recess 33, in order to engage the locking mechanism 18 of the associated interrupted threads 5, 14. In the locked position, the wedge device 35 is fitted into the recess 33 to secure the lever arm 25 against reverse rotation.

In the locked position, the bore 23 of the male connector 21 is also in alignment with the aperture 40 of the wedge device 35 so that the pin 41 can be screwed into the bore 23 as a further security measure to prevent reverse rotation of the connectors 21, 31 out of the engaged condition.

If the body component 20 needs to be replaced, the pin 41 can simply be unscrewed, the wedge device 35 removed and the lever arm 25 actuated to unlock the two connectors 21, 31, after which the body component 20 is free to be axially removed from the peg component 30.

An advantage of the bolt 22 and nut 32 configuration of FIGS. 5 to 11, is that the bolt 22 can be rotated independently of the implant body 13 so that there is no need to rotate the entire body component 20. Only the male connector 21 needs to be rotated about the axle 26 in order to engage the interrupted thread 5, 14 on each of the connectors 21, 31 and lock the components 20, 30 together.

Figure 12A:
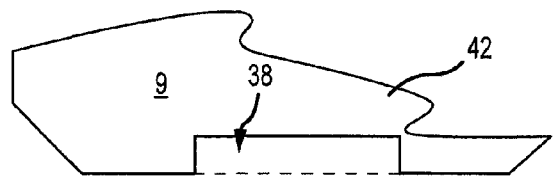
FIG. 12a is a profile view of a the extra wedge region of bone to be removed from the femur.
Figure 12B:
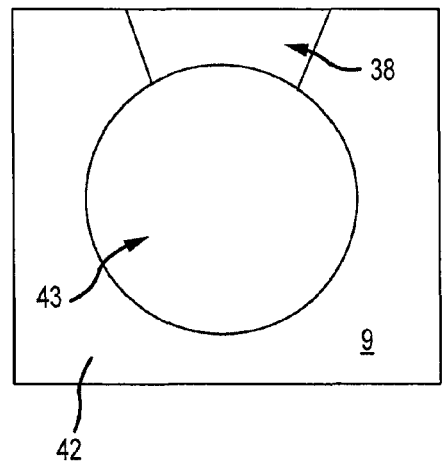
FIG. 12b is view of the underside of the femur showing the extra wedge of bone to be removed.

Referring now to FIG. 12a, a femur bone 50 is shown in profile. The femur bone 42, having already been machined to take the bone implant, is machined to remove the wedge shaped region 38 of bone 9, ready for receipt of the wedge device 35. As shown in FIG. 12b, a hole 43 is also formed in the bone for receipt of the peg component 30.

Figure 13:
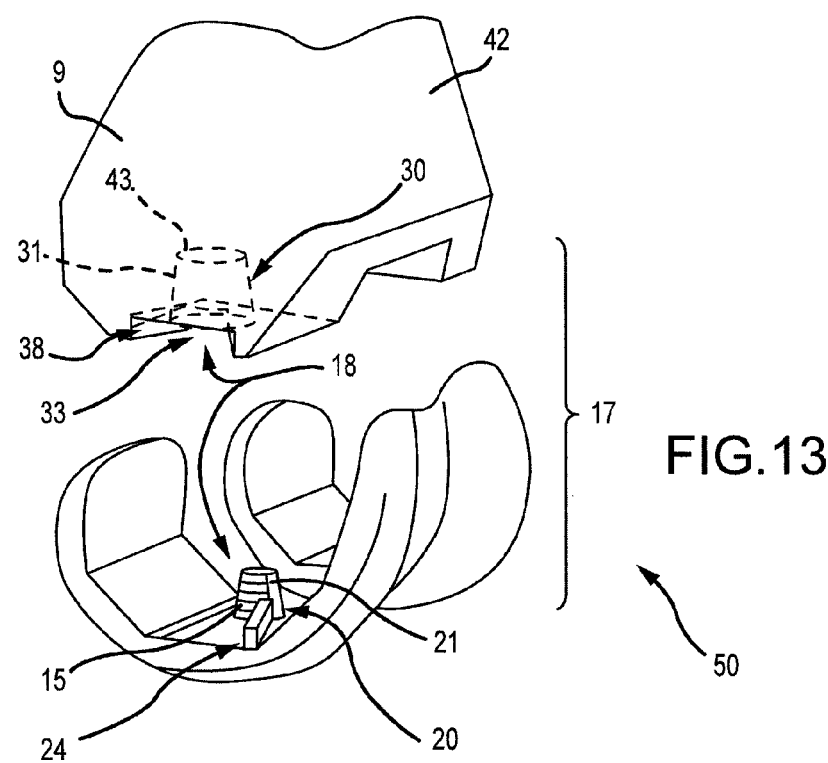

The prepared femur bone 42 is shown in perspective in FIG. 13, with the peg component 30 fitted into the hole 43 so that the recess 33 aligns with the region 38 of removed bone.

The body component 20 is illustrated beneath the femur bone 42, with the male connector 21 projecting from the implant body 13 (I don't think this is numbered in the drawing). To engage the two components 20, 30, the male connector 21 is inserted into the female connector 31 of the peg component 30 so that the actuator 24 is accessible though the removed region 38 of bone 9. Lever action is then exerted on the actuator 24 in order to rotate the male connector 21 and engage the lock mechanism 18 formed by the connected interrupted thread 5, 14 on each component 21, 31. The engaged components thereby form a coupling 17 to secure the peg component 30 to the body component 20. The wedge device 35 is then inserted into the recess 33 to prevent reverse rotation of the lever arm 25 and the locking pin 41 is screwed into the bolt 22 to lock the components 20, 30 together in order to form a complete bone implant 50.

If it becomes necessary to remove or replace the body component 20 of the implant 50, the wedge device 35 can be removed and interrupted threads 4, 15 simply disengaged, without the need to break the peg component 30 free of the bone 9. Since the peg component 30 is intended to be permanently affixed to the bone 9, additional mechanical anchoring mechanisms may be employed such as one way spikes to positively grip the bone, in combination with cement material or the like.

The bone implant 50 may also include multiple peg components 30 and a corresponding number of pairs of connectors 21, 31 to secure the body component 20 to the bone 9 and to assist in distributing load across the components 20, 30.

In relation to the use of interrupted thread 5, 14, a person skilled in the art would be able to readily determine the required thread design for differing mechanical needs, since the principles of interrupted thread design is well known and used in many industries such as in the design of breeches in ballistic weapons, where significant axial loads need to be accommodated.

Of course, alternative forms of engagement may be used for the connectors, however, the interrupted thread design is considered most suitable for the present invention as it allows reliable and high load coupling with only minimal relative movement between the connectors.

LIST OF PARTS

1. Peg component
2. Female connector
3. Nut
4. Cavity
5. Interrupted thread
6. Wall
7. Threaded section
8. Void
9. Bone
10. Body component
11. Male connector
12. Bolt
13. Implant body
14. Interrupted thread
15. Threaded section
16. Rebate
17. Coupling
18. Lock mechanism
19.
20. Body component
21. Male connector
22. Bolt
23. Bore
24. Actuator
25. Lever arm
26. Axle
27. End
28. Head
29.
30. Peg component
31. Female connector
32. Nut
33. Recess
34. End
35. Wedge device
36.
37. Surface
38. Region
39. Wedge piece
40. Aperture
41. Locking pin
42. Femur bone
43. Hole
50. Implant

The invention claimed is:

1. A bone implant including a plurality of peg components for fixing the implant into a bone, a body component for abutment with a mating bone implant and a plurality of couplings to allow releasable connection between each peg component and the body component;
   wherein each coupling includes a male connector and female connector that are moved into engagement by advancing one of said plurality of peg components into an engaged condition relative to the body component;
   wherein each female connector is a nut associated with one of said plurality of peg components and each male connector is a bolt associated with the body component;
   wherein each coupling includes a lock mechanism to secure the components in the engaged condition; and
   wherein the lock mechanism includes an interrupted thread on each of the connectors.

2. The bone implant of claim 1, wherein the lock mechanism further includes an actuator for rotating one of the connectors relative to the other connector in order to drive the interrupted thread on each connector into a locked engagement.

3. The bone implant of claim 2, wherein the actuator is in the form of a lever arm connected to one of the connectors.

4. The bone implant of claim 3, wherein the connector with the lever arm is mounted to the associated component via an axle that allows the connector to be rotated into locked engagement with the other connector without requiring the component itself to be rotated.

5. The bone implant of claim 3, wherein the implant further includes a wedge device to secure the lever arm against reverse rotation once the connectors are rotated into locked engagement.

6. The bone implant of claim 5, wherein a locking pin is provided to further secure the connectors against reverse rotation out of locked engagement, the locking pin being mounted relative to one of the connectors and being received in a bore formed in the other one of the connectors, wherein the bore aligns with the pin when the connectors are in locked engagement.

7. The bone implant of claim 6, wherein the locking pin is carried by the wedge device.

\* \* \* \* \*